(12) United States Patent
Shimizu (10) Patent No.: US 7,301,642 B2
(45) Date of Patent: Nov. 27, 2007

(54) APPARATUS AND METHOD OF ASSAY IN UTILIZING ATTENUATED TOTAL REFLECTION

(75) Inventor: Hitoshi Shimizu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 256 days.

(21) Appl. No.: 11/239,303

(22) Filed: Sep. 30, 2005

(65) Prior Publication Data
US 2006/0119852 A1  Jun. 8, 2006

(30) Foreign Application Priority Data
Sep. 30, 2004  (JP) .............................. 2004-288538

(51) Int. Cl.
*G01N 21/55* (2006.01)
*B01L 3/02* (2006.01)

(52) U.S. Cl. ....................................... 356/445; 422/100

(58) Field of Classification Search ........ 356/445–448, 356/246, 577; 755/100, 188, 98, 82.11; 436/518; 435/287.2
See application file for complete search history.

(56) References Cited

U.S. PATENT DOCUMENTS

| | | | |
|---|---|---|---|
| 4,650,477 A | 3/1987 | Johnson | |
| 4,871,683 A | 10/1989 | Harris et al. | |
| 5,313,264 A | 5/1994 | Ivarsson et al. | |
| 5,561,069 A * | 10/1996 | Brigham-Burke et al. | .. 436/518 |
| 5,822,073 A | 10/1998 | Yee et al. | |
| 7,193,703 B2 * | 3/2007 | Hakamata et al. | .......... 356/246 |
| 2006/0109472 A1 * | 5/2006 | Muraishi | ..................... 356/445 |
| 2006/0153742 A1 * | 7/2006 | Shimizu | ..................... 422/100 |
| 2006/0159591 A1 * | 7/2006 | Ohtsuka | ....................... 422/88 |
| 2006/0197954 A1 * | 9/2006 | Ogura et al. | ................. 356/445 |
| 2006/0257290 A1 * | 11/2006 | Shimizu | ..................... 422/100 |
| 2006/0263263 A1 * | 11/2006 | Shimizu | ..................... 422/100 |
| 2006/0263874 A1 * | 11/2006 | Kunuki et al. | ........... 435/287.2 |
| 2007/0054415 A1 * | 3/2007 | Muraishi | ..................... 436/518 |

FOREIGN PATENT DOCUMENTS

JP          6-167443 A       6/1994

* cited by examiner

*Primary Examiner*—Hoa Q. Pham
(74) *Attorney, Agent, or Firm*—Sughrue Mion, PLLC (57) ABSTRACT

A surface plasmon resonance (SPR) assay apparatus is loaded with a sensor unit. The sensor unit has a sensing surface and a flow channel, which has an entrance end opening and an exit end opening, and causes analyte fluid introduced through the entrance end opening to flow on the sensing surface. An optical assay unit assays reaction of the analyte fluid on the sensing surface by detecting attenuation of the illuminated light reflected by a thin film/dielectric interface. A fluid dispenser introduces the analyte fluid to the entrance end opening by pipetting. A fluid collecting vessel stores the analyte fluid used and exited from the exit end opening. A drain conduit extends from the exit end opening toward the fluid collecting vessel, for passage of the used analyte fluid. A suction pump drains the used analyte fluid into the fluid collecting vessel through the drain conduit.

18 Claims, 4 Drawing Sheets

APPARATUS AND METHOD OF ASSAY IN UTILIZING ATTENUATED TOTAL REFLECTION

BACKGROUND OF THE INVENTION

1. Field of the Invention

The present invention relates to an apparatus and method for assay in utilizing attenuated total reflection. More particularly, the present invention relates to an apparatus and method for assay in utilizing attenuated total reflection, in which a flow channel can be protected from backflow of waste fluid.

2. Description Related to the Prior Art

An assay apparatus in utilizing attenuated total reflection for assaying a sample is known in the field of the biosensor. U.S. Pat. No. 5,313,264 (corresponding to JP-A 4-501462) discloses a surface plasmon resonance (SPR) sensor as a typical example for this assay.

A thin film, or metal film, is formed on a transparent dielectric medium. One surface of the metal film is a sensing surface where reaction of a sample occurs. Another surface of the metal film is a thin film/dielectric interface where light is applied by satisfying a condition of total reflection. The reaction is detected to assay the sample according to attenuation of the reflected light from the thin film/dielectric interface. In a surface plasmon resonance (SPR) sensor, surface plasmon is a term to mean the compressional wave created on the surface of the metal and included in plasmon as quantized expression of the compressional wave. Free electrons in a metal vibrate to generate the compressional wave.

The surface plasmon resonance (SPR) assay apparatus is constructed to detect surface plasmon resonance created on the sensing surface which is a first surface of the metal film, and along which the surface plasmon travels.

Light for detection is applied to a thin film/dielectric interface of the metal film that is back to the sensing surface so that the total reflection condition is satisfied, namely at an angle of incidence equal to or more than a critical angle. In addition to the total reflection created on the thin film/dielectric interface, a small component of the light passes through the metal film without reflection, and penetrates to the sensing surface. A wave of the penetrating component is called an evanescent wave. Surface plasmon resonance (SPR) is created when frequency of the evanescent wave coincides with that of the surface plasmon. In response to this, intensity of the reflected light attenuates remarkably. In the assay apparatus, the attenuation in the reflected light reflected by the thin film/dielectric interface is detected, to recognize creation of the SPR on the sensing surface.

The angle of incidence, namely resonance angle of the light to generate the SPR depends on the refraction index of the transmission medium transmitting evanescent wave and surface plasmon. In other words, a change in the resonance angle to create SPR changes in response to a change in the refraction index of the transmission medium. The substance contacting the sensing surface is a transmission medium transmitting the evanescent wave and surface plasmon. If binding or dissociation between two molecules occurs on the sensing surface, the resonance angle changes because of a change in the refraction index of the transmission medium. In the SPR system, the change in the refraction index is detected, to measure interaction of molecules.

The assay apparatus can be used for various kinds of studies in a biochemical field or the like, for example to study interaction of protein, DNA and various biomaterials, and to select candidate drugs by screening. Also, the technique is useful in the fields of the clinical medicine, food industries and the like. It is possible to use one of two substances as a ligand and another of them as an analyte if those have bioaffinity. For the purpose of screening, protein as biomaterial is used as ligand. Candidate drugs are discretely used as analyte, and contacted with the ligand on the sensing surface, to study interaction.

JP-A 6-167443 and U.S. Pat. No. 5,822,073 disclose an SPR assay apparatus in which an optical system of Kretschmann configuration is used for incidence of light to the metal film. According to the Kretschmann configuration, the thin film/dielectric interface of the metal film is fitted on a prism, which condenses light and directs the light to the thin film/dielectric interface in a manner conditioned for total reflection. A sample or ligand is immobilized on the sensing surface. A flow channel is formed to have the sensing surface inside, and causes analyte fluid to flow. The analyte fluid is introduced in the flow channel to flow, and is caused to contact the ligand. Interaction between the analyte fluid and the ligand is assayed by detecting surface plasmon resonance created during the reaction.

At first in an assay, liquid buffer is introduced to a flow channel to contact a sensing surface. An output signal starts being measured with the buffer. Then analyte fluid is introduced. The liquid buffer in the flow channel is pushed out by the analyte fluid, and is drained through an exit end opening of the flow channel. The analyte fluid is kept to exist in the flow channel for a prescribed time, before the liquid buffer is introduced again. Then the measurement of the output signal is completed. According to detection of a base line of the output signal, detection is possible during a process starting at association between the analyte and ligand and ending at dissociation between those.

Examples of methods for introducing the analyte fluid on to the sensing surface includes delivery by means of conduits and pumps, and delivery through a pipette couple. The pipette couple is easily settable on end openings of the flow channel, and suitable for access to numerous sensor cells by loading and unloading at many times. Specifically, a dispensing pipette included in the pipette couple is set at the flow channel for dispensing the analyte fluid. A removing pipette included in the pipette couple removes the liquid buffer through the flow channel through the exit end opening by suction.

However, there is a problem in the method of the pipette couple. After the introduction, the liquid buffer from the exit end opening is likely to leak from the end of the removing pipette upon unloading of the pipette couple. Droplets of the liquid buffer will enter the exit end opening to flow back through the flow channel. A backflow of the liquid buffer causes a serious problem in electric noise in an output signal of the assay.

SUMMARY OF THE INVENTION

In view of the foregoing problems, an object of the present invention is to provide an apparatus and method for assay in utilizing attenuated total reflection, in which a flow channel can be protected from backflow of waste fluid.

In order to achieve the above and other objects and advantages of this invention, an assay apparatus for assay in utilizing attenuated total reflection is provided, by use of a sensor unit including a transparent dielectric medium, and a thin film, having a first surface and a sensing surface reverse thereto, the first surface being connected with the dielectric medium to constitute a thin film/dielectric interface, wherein a flow channel is used, has an entrance end opening and an exit end opening, and causes sample fluid introduced through the entrance end opening to flow on the sensing surface, there being an optical assay unit for traveling of illuminating light to the interface in a form satisfying a total reflection condition, and for assaying reaction of the sample fluid on the sensing surface by detecting attenuation of the illuminated light reflected by the interface. The assay apparatus includes a fluid dispenser for introducing the sample fluid to the entrance end opening. A fluid collecting vessel stores the sample fluid used and exited from the exit end opening. A drain conduit is disposed to extend from the exit end opening toward the fluid collecting vessel, for passage of the used sample fluid. A suction device drains the used sample fluid into the fluid collecting vessel by suction thereof through the drain conduit.

Preferably, the suction device prevents the used sample fluid from flowing back through the exit end opening, to suppress decrease in measuring precision of the optical assay unit.

Preferably, the drain conduit has an upstream end disposed at a predetermined interval from the exit end opening.

Preferably, the suction device decompresses gas inside the fluid collecting vessel by use of negative pressure for the suction, for the used sample fluid to flow through the drain conduit toward the fluid collecting vessel.

Furthermore, a controller controls the suction device for suction sequentially according to start and stop of the fluid dispenser introducing the sample fluid.

Preferably, the sensor unit includes a fluid reserving chamber formed to communicate serially with the exit end opening, for reserving the used sample fluid. The drain conduit has an upstream end disposed within the fluid reserving chamber.

Preferably, the controller starts the suction device for suction sequentially in compliance with starting of the fluid dispenser to introduce the sample fluid, and stops the suction device from suction sequentially in compliance with stopping of the fluid dispenser from introducing the sample fluid.

Preferably, the sensor unit further includes a flow channel assembly having the flow channel formed therein. The fluid reserving chamber is formed in the flow channel assembly, is open and positioned at the exit end opening, and extends in a larger size than the exit end opening.

Preferably, the flow channel assembly includes a flow channel block having the flow channel. An additional block is secured to an upside of the flow channel block, and has the fluid reserving chamber and an additional orifice open and positioned at the entrance end opening.

Furthermore, a switching valve is connected in a middle of the drain conduit, for being open and closed to change over drainage of the used sample fluid.

Preferably, the drain conduit includes an upstream conduit portion disposed to extend from the flow channel to the switching valve. A downstream conduit portion is disposed to extend from the switching valve to the fluid collecting vessel. The switching valve includes an intake port for intake of external gas into a valve chamber. A shiftable mechanism changes over between the upstream conduit portion and the intake port, connects the upstream conduit portion with the downstream conduit portion when in a connection position, to cause the used sample fluid to flow, and disconnects the upstream conduit portion from the downstream conduit portion by communication of the intake port with the downstream conduit portion when in a disconnection position.

Furthermore, a moving mechanism moves an upstream end of the drain conduit, to change over the upstream end between connection and disconnection with the exit end opening.

Furthermore, a carriage is slidable up or down by the moving mechanism, for supporting the upstream end of the drain conduit to set the upstream end on the sensor unit.

Preferably, the carriage includes a block portion, provided with the fluid dispenser secured thereto, for being driven by the moving mechanism. A board portion is disposed to extend from the fluid dispenser, for supporting the upstream end of the drain conduit.

Preferably, the fluid dispenser is a pipetting type.

In one aspect of the invention, an assay method of assay in utilizing attenuated total reflection by use of a sensor unit is provided. The assay method includes a step of sucking the sample fluid used and exited from the exit end opening. Then the used sample fluid sucked to flow is drained into a fluid collecting vessel.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1A:
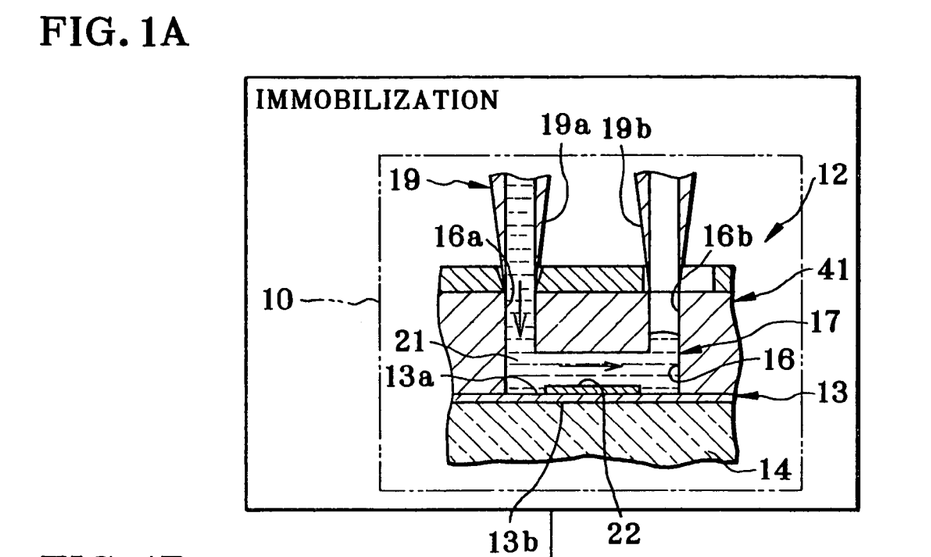
FIG. 1A is a section, partially broken, illustrating a sample immobilizing step included in an assay method of a surface plasmon resonance biosensor.
Figure 1B:
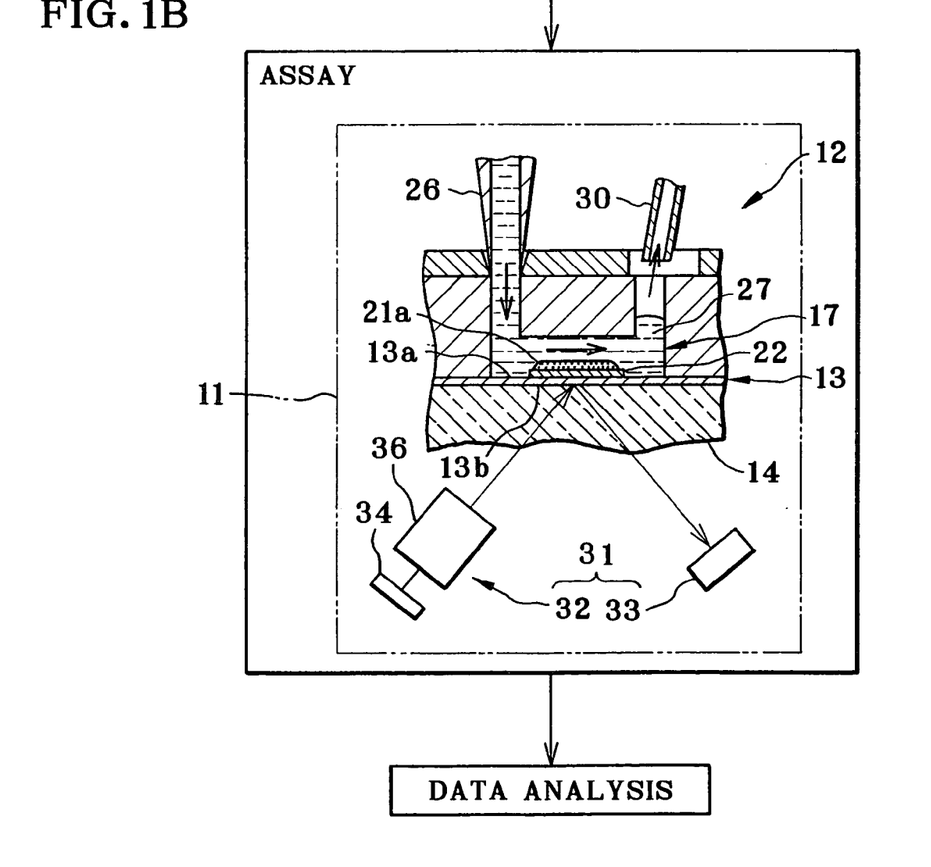
FIG. 1B is a section, partially broken, illustrating an assay step included in the assay method.

In FIGS. 1A and 1B, a system for measuring or assay according to SPR (surface plasmon resonance) is illustrated. A sequence of the assay system is constituted by three processes which are a sample immobilizing process, assay process and data analyzing process. The assay system includes a sample immobilizing device 10, an assay apparatus 11, and a data analyzer.

A surface plasmon resonance (SPR) biosensor is used as a sensor unit 12 for assay. The sensor unit 12 includes a metal film 13, a prism 14 and a flow channel block 41. A first surface of the metal film 13 is a sensing surface 13a where surface plasmon resonance is created. A second surface of the metal film 13 is a thin film/dielectric interface 13b where the prism 14 is overlaid therewith. The flow channel block 41 has a flow channel 16, which extends along the sensing surface 13a, and causes ligand and analyte as fluids to flow.

An example of material for the metal film 13 is gold (Au). A thickness of the metal film 13 is 50 nm. The thickness can be changed for the suitability in view of the material of the metal film 13, a wavelength of light to be applied, and the like. The prism 14 is a transparent dielectric medium or block, overlaid with the metal film 13, and also is an optical element for condensing light toward the thin film/dielectric interface 13b for satisfying the condition of the total reflection. The flow channel 16 is a U-shaped conduit, and has an entrance end opening 16a and an exit end opening 16b. A diameter of the flow channel 16 is approximately 1 mm. An interval between the entrance end opening 16a and the exit end opening 16b is approximately 10 mm.

A lower side of the flow channel 16 is open initially, but closed in a firmly enclosed manner by covering of the sensing surface 13a. Sensor cells 17 are constituted by combinations of the flow channel 16 and the sensing surface 13a.

The immobilizing process is a binding step of ligand on the sensing surface 13a. At first, the sensor unit 12 is set in the sample immobilizing device 10. A pipette couple 19 is included in the sample immobilizing device 10, and has dispensing and removing pipettes 19a and 19b. The dispensing pipette 19a is set at the entrance end opening 16a. The removing pipette 19b is set at the exit end opening 16b. The dispensing pipette 19a introduces liquid to the flow channel 16. The removing pipette 19b sucks and removes liquid from the flow channel 16. The introduction with the dispensing pipette 19a is at the same time as the removal with the removing pipette 19b. Ligand solution or ligand fluid 21, as a fluid which contains ligand or biomaterial and fluid medium, is introduced through the entrance end opening 16a by the pipette couple 19.

A linker film 22 is overlaid on a middle portion of the sensing surface 13a for binding with the ligand. In the manufacturing process of the sensor unit 12, the linker film 22 is formed. As the linker film 22 is a basis for immobilizing the ligand, a material for the linker film 22 is selectively determined.

Pre-treatment before immobilization with the ligand fluid 21 is wetting of the linker film 22 by use of liquid buffer, and activation of the linker film 22 for the purpose of facilitating binding of the ligand to the linker film 22. An example of a method is the amine coupling method. An example of material for the linker film 22 is carboxy methyl dextran, to bind an amino group contained in the ligand with the dextran directly by a covalent bond. An example of liquid for the activation is mixture of N'-(3-dimethylaminopropyl) carbodiimide hydrochloride (EDC) and N-hydroxy imide succinate (NHS). After the activation, liquid buffer for immobilization is introduced to wash and clean the flow channel 16.

Various liquids are available for use as the liquid buffer for immobilization, and solvent or diluent for the ligand fluid 21. Examples of the liquids include buffer liquids, or physiological saline water and other aqueous solutions of physiological salts, and pure water. It is possible according to a type of the ligand to determine suitably solution types and pH values of the solutions, and types of substances to be mixed, and their density. If a biomaterial is used as a ligand, physiological saline water is used of which pH value is kept neutralized. In the amine coupling method described above, the linker film 22 is electrified negatively because of the carboxy methyl dextran. In consideration of this, it is possible to use phosphate buffered saline (PBS) solution having strong operation of buffer and containing phosphate salt at high density which is not physiological, because protein can be electrified positively for the purpose of facilitating binding with the linker film 22.

After the activation and washing, the ligand fluid 21 is introduced to the sensor cells 17 for a ligand immobilizing process. Ligand or sample 21a such as biomaterial diffused in the ligand fluid 21, in introducing the ligand fluid 21, gradually comes near to and binds with the linker film 22. This is immobilization of the ligand 21a on the sensing surface 13a. It is general that a step of the immobilization requires approximately one (1) hour, during which the sensor unit 12 is preserved in an environment conditioned suitably, for example at a conditioned temperature. In the course of the immobilization, the ligand fluid 21 in the flow channel 16 may be left to stand in a stationary state. However, the ligand fluid 21 can be preferably stirred or turbulently flowed for ensured fluidity in the flow channel 16. The stirring or turbulent flow can promote binding of the ligand 21a with the linker film 22, to raise an immobilized amount of the ligand 21a.

When the immobilization of the ligand 21a on the sensing surface 13a is completed, then the ligand fluid 21 is removed from the flow channel 16. The removing pipette 19b discharges the ligand fluid 21 by suction. After this, the sensing surface 13a is washed by feeding washing liquid into the flow channel 16. A blocking step, if required, is added after the washing. A blocking liquid is introduced into the flow channel 16, to render inactive the reaction group remaining without binding with the ligand. A preferable example of the blocking liquid is ethanol amine hydrochloride. After the blocking, the flow channel 16 is washed again. Then evaporation retardant is introduced to the flow channel 16, which will be described in detail later. The sensor unit 12 remains preserved until the assay with the sensing surface 13a humid on the evaporation retardant.

For the assay process, the sensor unit 12 is set in the assay apparatus 11. A pipette couple 26 is disposed in the assay apparatus 11. A dispensing pipette in the pipette couple 26 introduces liquid of several types into the flow channel 16 through the entrance end opening 16a.

For the assay, at first, liquid buffer is introduced into the flow channel 16, and caused to flow continuously for a prescribed time. After this, analyte solution or analyte fluid 27, as a fluid which contains analyte and fluid medium that may be solvent, is introduced into the flow channel 16. The introduction of the analyte fluid 27 drains the liquid buffer from the flow channel 16 by substitution. The analyte fluid 27 is caused to flow continuously for a prescribed time, before liquid buffer is introduced again for assay. There is a drain conduit 30 which drains the waste fluid exited from the exit end opening 16b by suction, so as to collect the analyte fluid and liquid buffer as waste. Note that the flow channel 16 may be cleaned or washed before initially introducing the liquid buffer.

Reading of data starts upon initially introducing the liquid buffer in order to detect a reference level of a signal. The reading is continued until the introduction of the liquid buffer at the second time after entry of the analyte fluid 27. It is possible not only to detect the reference level but to assay interaction or binding between the analyte and the ligand, and to measure a signal until dissociation between the analyte and ligand in response to introduction of the liquid buffer.

Various liquids are available for use as the liquid buffer for assay, and solvent or diluent for the analyte fluid 27. Examples of the liquids include buffer liquids, or physiological saline water and other aqueous solutions of physiological salts, and pure water. It is possible according to a type of a ligand to determine suitably solution types and pH values of the solutions, and types of substances to be mixed, and their density. To facilitate dissolving of the analyte, dimethyl sulfo-oxide (DMSO) can be added to the physiological saline water. The use of the DMSO is reflected to a level of an output signal. The buffer for assay is used for detecting the reference level of the signal, as described above. If DMSO is contained in the solvent for the analyte, it is preferable to use buffer for assay at a DMSO density approximately equal to that of the solvent in the analyte.

In general, the analyte fluid 27 may be kept preserved for a long time, for example one year. It is likely that a difference occurs between an initial level and a current level of the DMSO density owing to a change with time. If assay with high precision is required, such a difference in the density is estimated according to the ref-signal level upon introducing the analyte fluid 27, so that measured data can be compensated for by DMSO density compensation.

A ref-signal and an act-signal are SPR output signals. A measuring region (act) on the sensing surface 13a has immobilization of a ligand, and is a region for reaction between the ligand and analyte. A reference region (ref) on the sensing surface 13a does not have immobilization of a ligand, and is used for outputting a ref-signal for comparison with a signal retrieved from the measuring region (act). Data analysis is effected by obtaining a difference or ratio of the act-signal and ref-signal. For example, the data analyzer obtains data of a finite difference between the act-signal and ref-signal, and analyzes various items according to the finite difference. This makes it possible to cancel electric noise caused by external irregularities, such as individual specificity of sensor units or sensor cells, mechanical changes of the assay apparatus, temperature changes of the liquid, and the like. A signal with a high S/N ratio can be obtained.

Compensation data for the DMSO density compensation is obtained before introducing the analyte fluid 27. A plurality of liquid buffers different in the DMSO density are introduced to the flow cells 17. Amounts of changes in the levels of ref-signal and act-signal are evaluated so as to obtain the compensation data.

An optical measuring unit or optical assay unit 31 is disposed in the assay apparatus 11. An illuminator 32 and a photo detector 33 are included in the optical assay unit 31. The reaction between the ligand and analyte can be recognized as a change of a resonance angle, which is an angle of incidence of light received by the thin film/dielectric interface 13b. To this end, the illuminator 32 is caused to apply light to the thin film/dielectric interface 13b at various values of angles of incidence satisfying a condition of the total reflection. The illuminator 32 includes a light source device 34 and an illuminating optical system 36, which includes a condensing lens, a diffusing plate and a polarizer. A position and angle of the installation of those elements are so determined that an angle of incidence of the light satisfies the condition of the above total reflection.

Examples of the light source device 34 include a light emitting diode (LED), laser diode (LD), super luminescent diode (SLD), and other light emitting element. A single element is used as the light source device 34 as a point light source. If simultaneous assay for plural sensor cells is described, light from a single light source can be separated to illuminate the plural sensor cells. Also, a plurality of elements as the light source device 34 may be arranged as a surface light source. The diffusing plate diffuses light from the light source device 34, and suppresses onset of irregularity in the light amount. The polarizer allows only p-polarized light to pass, the p-polarized light creating the surface plasmon resonance. Note that no polarizer is required if directions of rays emitted by the light source device 34, for example an LD, are kept equal. However, a diffusing plate may be combined with the light source device 34 of a type of which directions of emitted rays are kept equal. Directions of rays in polarization are changed unequal by the passage through the diffusing plate. For this structure, the polarizer can be utilized to set equal the directions of the rays. The light obtained after the diffusion and polarization is condensed by a condensing lens, and directed to the prism 14. It is possible to travel rays with various angles of incidence toward the thin film/dielectric interface 13b without irregularity in the intensity.

The photo detector 33 receives light reflected by the thin film/dielectric interface 13b, and detects intensity of the light. Rays of light are incident upon the interface 13b at various angles. It follows that light is reflected by the interface 13b at various angles of reflection according to the angles of the incidence. If there is a change in the resonance angle of the medium on the sensing surface 13a, a refraction angle changes. If there is interaction of the analyte and ligand, a reflection angle at which light is attenuated is changed by the change in the resonance angle.

An example of the photo detector 33 is a CCD area sensor or an array of photo diodes, which retrieves such a change in the reflection angle as a gradual change in the attenuating position of the reflected light by a photo receptor surface. The interaction between the ligand and analyte is recognized as information of shifting of a position of attenuation of the reflected light on the photo reception surface. The media in contact with the sensing surface 13a becomes different between the states before and after the contact of the ligand with the analyte. Also, the position of the attenuation of the reflected light changes, and thus the resonance angle at which surface plasmon resonance occurs changes between those states. When reaction starts by contact between the analyte and ligand, the resonance angle starts changes, to start shifting the attenuation position of the reflected light on the photo reception surface. The photo detector 33 generates measured data which is information of the interaction, and sends the measured data to the data analyzer. The data analyzer analyzes the measured data from the assay apparatus 11, to retrieve a characteristic and other information of the analyte.

Figure 2:
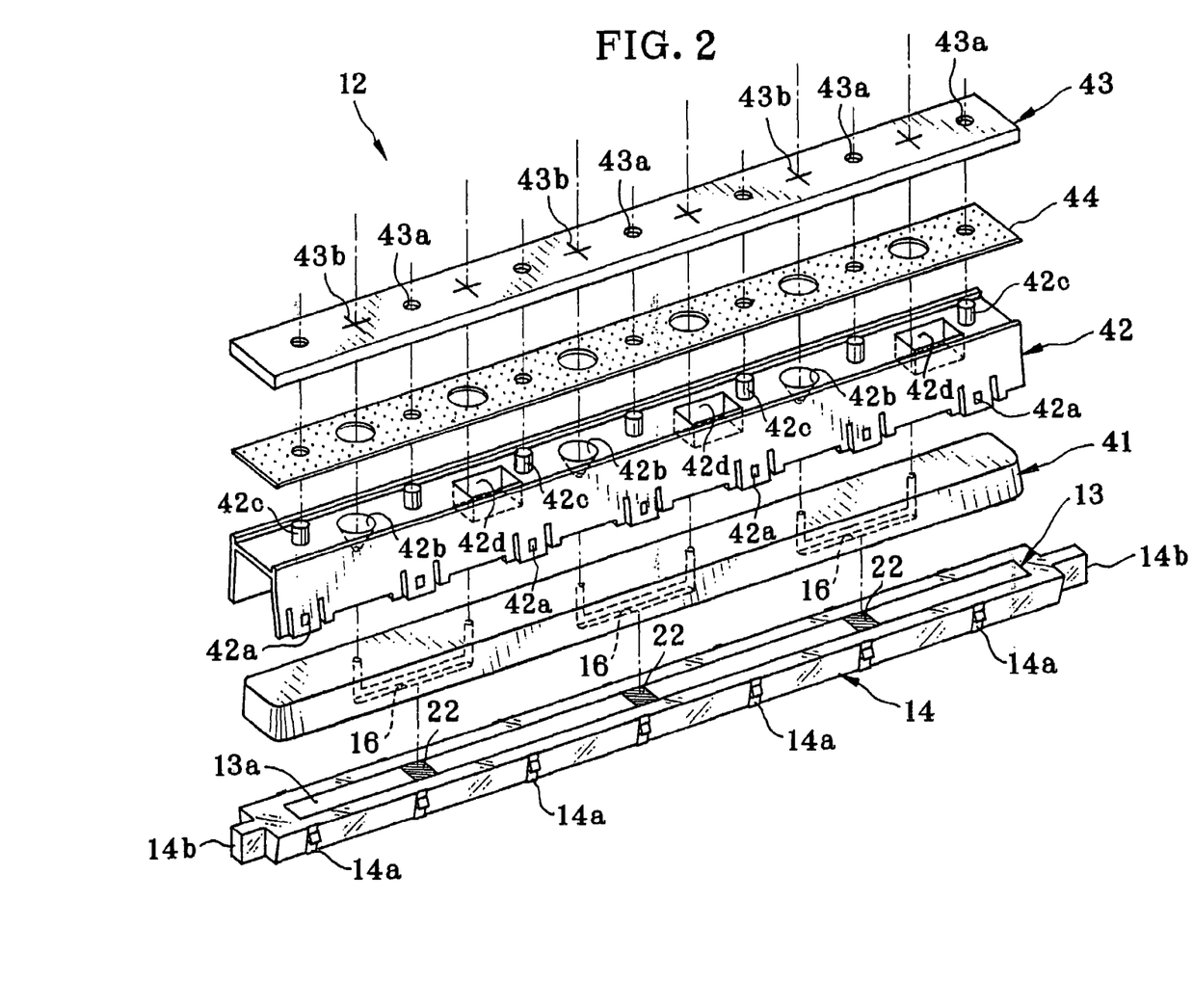
FIG. 2 is an exploded perspective illustrating a sensor unit.

Note that in FIG. 2, the illuminator 32 and the photo detector 33 in the optical assay unit 31 are positioned so that a direction of light projected and reflected between those intersects horizontally with a flow of the flow channel 16, which is unlike the structure depicted in FIG. 1B. The state of FIG. 1B is simplified for the convenience. However, in the invention the illuminator 32 and the photo detector 33 may be positioned according to in FIG. 1B so that a direction of light projected and reflected between those is horizontally aligned with the flow of the flow channel 16 between the pipettes.

In FIG. 2, the sensor unit 12 is illustrated structurally. The sensor unit 12 includes the flow channel block 41, the prism 14, an additional block 42, and a lid 43. The flow channel block 41 has the at least one flow channel 16 formed through the same. The prism 14 has the metal film 13 overlaid on its upper surface. The additional block 42 supports the flow channel block 41 by fitting its lower surface on an upper surface of the prism 14. The lid 43 is disposed higher than the additional block 42.

The flow channel 16, for example three (3) channels, are formed in the flow channel block 41. The flow channel block 41 has a long shape, in which the flow channels 16 are arranged in a direction of a block length. The flow channels 16 constitute the sensor cells 17 together with the metal film 13 in connection with its lower surface. See FIGS. 1A and 1B. The flow channel block 41 is formed from elastic material for the purpose of ensuring tightness in contact with the metal film 13. Examples of elastic materials include rubber, polydimethylsiloxane (PDMS), and the like. When a lower surface of the flow channel block 41 is pressed on an upper surface of the prism 14, the flow channel block 41 is elastically deformed, to remove a space between its surface and the metal film 13. Open lower portions of the flow channels 16 are closed water-tightly by the upper surface of the prism 14. Note that the number of the flow channels 16 may not be three, but can be one or two, or four or more.

The metal film 13 is deposited on the prism 14 by vapor deposition. The metal film 13 is formed in plural regions of long quadrilaterals opposed to the flow channel 16 formed in the flow channel block 41. Also, the linker film 22 is overlaid on an upper face or the sensing surface 13a of the metal film 13 and in regions associated with the flow channels 16. Retaining claws 14a are formed to project from the prism 14 at its sides as viewed longitudinally. Retaining claws 42a of the additional block 42 are engageable with the retaining claws 14a. The flow channel block 41 is sandwiched between the additional block 42 and the prism 14. A lower surface of the flow channel block 41 is kept fitted on the prism 14. A composite part as biosensor is obtained by unifying the flow channel block 41, the metal film 13 and the prism 14.

Retaining projections 14b protrude from ends of the prism 14 as viewed in its longitudinal direction. A sensor holder contains a plurality of sensor units 12. The retaining projections 14b are formed for positioning the sensor unit 12 in a contained state by engagement with the sensor holder.

An additional orifice 42b is formed in the additional block 42, and positioned at each of the entrance end opening 16a and the exit end opening 16b of the flow channel 16, for entry of an end of each of dispensing and removing pipettes 26a and 26b and the dispensing and removing pipettes 19a and 19b. The additional orifice 42b has a funnel shape for introducing liquid ejected by the pipettes toward the entrance end opening 16a. A fluid reserving chamber 42d is formed in the sensor unit 12, positioned at respectively the exit end opening 16b of the flow channel 16, for reserving used sample fluid or waste fluid 90 exited from the exit end opening 16b through the flow channel 16. The fluid reserving chamber 42d stores the used sample fluid 90 in a temporary manner from the exit end opening 16b to prevent the fluid from scattering externally around the sensor unit 12. During the introduction of fluid for the immobilization, the fluid reserving chamber 42d receives insertion of the removing pipette 19b. For the assay, the drain conduit 30 is inserted in the fluid reserving chamber 42d. The fluid having reached the fluid reserving chamber 42d are sucked by the removing pipette 19b or the drain conduit 30 and removed for withdrawal.

Note that it is possible in the immobilizing introduction to reserve the ligand liquid in the fluid reserving chamber 42d, and flow the same back to the flow channel 16 so as to introduce the ligand fluid again on to the sensing surface 13a. Thus, fluidity of the ligand fluid can be high inside the flow channel 16, so as to raise efficiency in the immobilization.

When the additional block 42 becomes engaged with the prism 14 together with the flow channel block 41, a lower face of the additional orifice 42b becomes connected with the entrance end opening 16a of the flow channel 16 for flow of fluid. The fluid reserving chamber 42d becomes connected with the exit end opening 16b of the flow channel 16 for flow.

Cylindrically shaped bosses 42c are formed to project beside the additional orifice 42b. Positioning holes 43a are formed in the lid 43. The bosses 42c are fitted in the positioning holes 43a, to position the lid 43 firmly. Double-sided adhesive tape 44 attaches the lid 43 to an upper surface of the additional block 42. Note that suitable holes are formed in the double-sided adhesive tape 44 and associated with the additional orifice 42b and the bosses 42c.

The lid 43 covers the additional orifice 42b communicating to the flow channel 16, and prevents evaporation of liquid in the flow channel 16. The lid 43 is formed from rubber, elastomer, resin or other elastic material. A cross shaped slit 43b is formed in the lid 43 and positioned respectively at the additional orifice 42b. The lid 43 is required to cover the additional orifice 42b in order to prevent liquid in the flow channel 16 from evaporation. However, no pipette can enter the additional orifice 42b if covering of the lid 43 is complete. So the cross shaped slit 43b is formed to enable insertion of pipettes, and to close the additional orifice 42b while no pipette is inserted. If a pipette is forcibly pressed into the cross shaped slit 43b, its edges are elastically deformed, to allow receipt of the pipette by becoming open. See FIGS. 1A and 1B. When the pipette is externally pulled out, the cross shaped slit 43b elastically closes the additional orifice 42b again by returning to its initial state.

Figure 3:
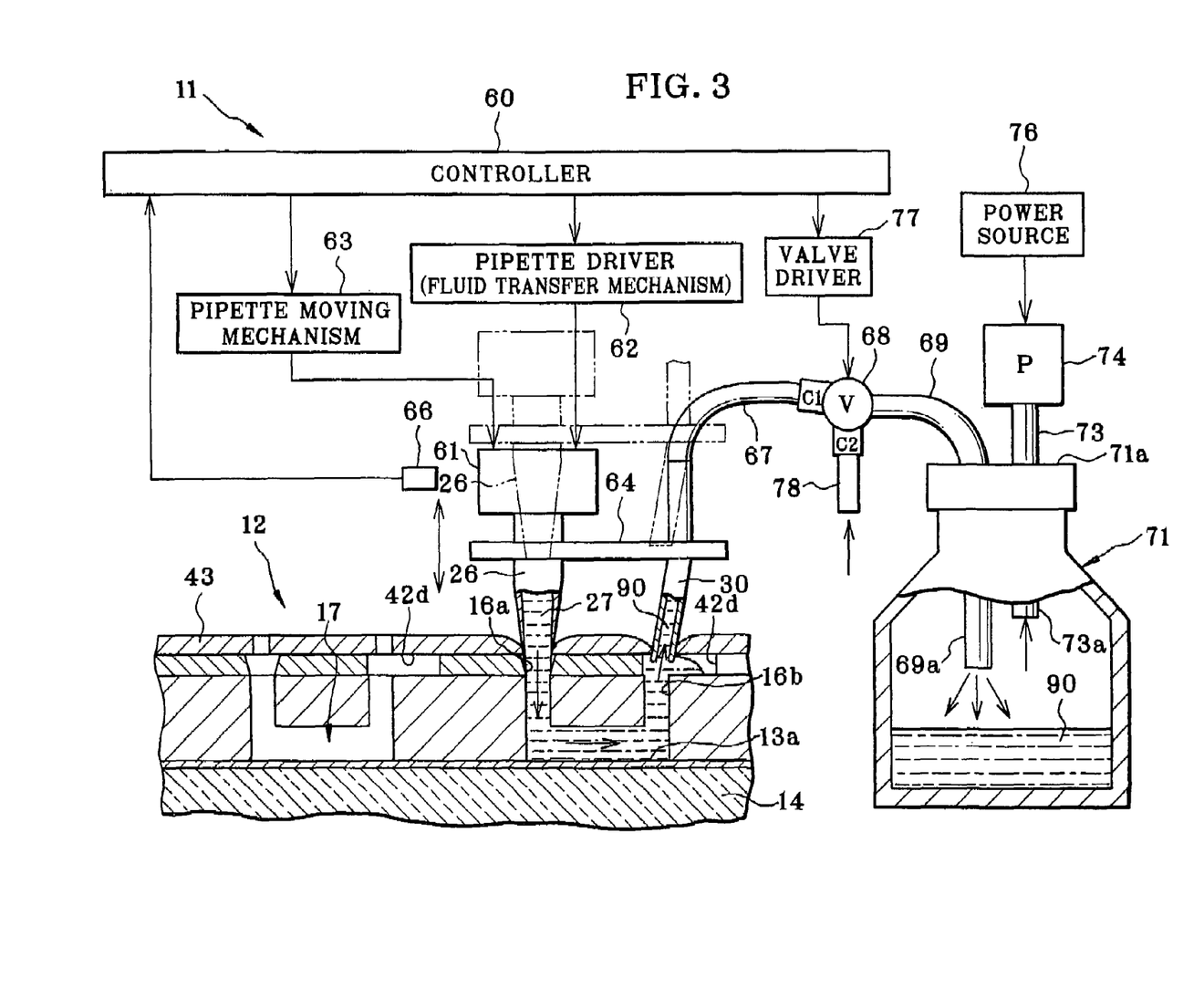
FIG. 3 is an explanatory view illustrating relevant elements in the assay apparatus for draining used sample fluid.

In FIG. 3, the assay apparatus 11 is schematically illustrated. A controller 60 controls various elements of the assay apparatus 11. A body or block portion 61 of a carriage supports the pipette couple 26, and contains a fluid transfer mechanism for driving a piston of the pipette couple 26. A pipette driver 62 as fluid transfer mechanism is controlled by the controller 60, and causes dispensation of fluid through the pipette couple 26. A pipette moving mechanism 63 keeps the pipette couple 26 movable in horizontal and vertical directions. The pipette moving mechanism 63 is controlled by the controller 60. The controller 60 enables the pipette moving mechanism 63 to access any selected one of the sensor cells 17. The pipette couple 26 is vertically movable and between a dispensing position and an initial position, and when in the dispensing position, sets its dispensing end at the entrance end opening 16a for introduction of fluid to the metal film 13, and when in the initial position, comes higher than the dispensing position for retraction. There is a board portion 64 of the carriage where the both of the pipette couple 26 and the drain conduit 30 are positioned. When the pipette couple 26 moves, the drain conduit 30 moves similarly and together. When the pipette couple 26 comes to the dispensing position, an upstream end of the drain conduit 30 comes to the fluid reserving chamber 42d.

A photo sensor 66 as position sensor detects shifting of the pipette couple 26 from the initial position to the dispensing position. An example of the photo sensor 66 is a reflection type photo sensor, which has a light projector and a photo reception surface oriented equally to each other. Detecting light is projected by the light projector, and upon being reflected by an object, is sensed by the photo reception surface. An example of the position of the photo sensor 66 is such that the body or block portion 61 of the pipette couple 26 comes in a light path of the photo sensor 66 when the pipette couple 26 comes down to the dispensing position. The photo sensor 66, upon detecting entry of the block portion 61, sends a detection signal to the controller 60. The controller 60 is responsive to the detection signal, and recognizes the reach of the pipette couple 26 to the dispensing position. Note that a photo interrupter may be used, which includes a light projector and a photo reception surface opposed thereto. For use with the photo interrupter, a blocking segment for passage between the light projector and the photo reception surface should be disposed in the block portion 61, to detect the passage of the pipette couple 26.

There is an upstream conduit portion or hose 67 in the drain couduit. An electromagnetic valve 68 as switching valve is connected with the drain conduit 30 by the upstream conduit portion 67. The upstream conduit portion 67 is flexible in response to shifting of the pipette couple 26. There is a downstream conduit portion or tube 69 in the drain couduit. A fluid collecting vessel 71 is connected with the electromagnetic valve 68 by the downstream conduit portion 69. A pipe fitting or packing 71a is secured to the top of the fluid collecting vessel 71. A conduit end 69a of the downstream conduit portion 69 is fitted in the pipe fitting 71a and extends to the inside of the fluid collecting vessel 71. The fluid collecting vessel 71 collects used sample fluid or waste fluid 90 removed by suction through the drain conduit 30, the upstream conduit portion 67, and the downstream conduit portion 69. A conduit end 73a of an exhaust port or tube 73 is inserted in the pipe fitting 71a of the fluid collecting vessel 71. A suction pump 74 as suction device is connected with a second conduit end of the exhaust port 73. The pipe fitting 71a of the fluid collecting vessel 71 is sealed so as to preventing entry of external air except for the downstream conduit portion 69 and the exhaust port 73. So the inside of the fluid collecting vessel 71 is enclosed.

An example of the suction pump 74 is a vacuum pump. A power source 76 is connected with the suction pump 74, which is responsive to turning on of a main switch of the assay apparatus 11, to start operation of suction. When the main switch is turned off, the suction pump 74 stops operating. The suction pump 74 in operation sucks air or other gas from the inside of the fluid collecting vessel 71 through the exhaust port 73. Negative pressure is applied to the inside of the fluid collecting vessel 71. The drain conduit 30 sucks and removes the fluid in the fluid reserving chamber 42d. The fluid is caused to flow through the upstream and downstream conduit portions 67 and 69, and collected by the fluid collecting vessel 71.

A fluid path C1 in the electromagnetic valve 68 communicates with the upstream conduit portion 67. A fluid path C2 in the electromagnetic valve 68 communicates with an intake port or conduit or tube 78. A valve driver 77 drives the electromagnetic valve 68. The controller 60 controls the electromagnetic valve 68 by means of the valve driver 77. The suction pump 74 continues decompression while the main switch is turned on. The drainage through the drain conduit 30 is started and stopped by the electromagnetic valve 68.

A mechanical structure is so provided that a first one of the two fluid paths C1 and C2 is closed when a second one of those is opened. When the fluid path C1 is opened, the intake port or conduit 78 is closed at the fluid path C2 to block intake of external gas. A path between the drain conduit 30 and the downstream conduit portion 69 opens to start drainage by suction. When the fluid path C1 is closed, the port between the drain conduit 30 and the downstream conduit portion 69 is closed to discontinue drainage by suction. The fluid path C2 opens in turn. The suction pump 74 continues suction irrespective of the open or closed state of the fluid paths C1 and C2, and thus causes external gas to flow into the fluid collecting vessel 71 through the intake port 78 by opening the fluid path C2.

The intake port or conduit 78 has a smaller diameter than that of the downstream conduit portion 69 or the exhaust port 73. When the fluid path C2 is unstopped in suction of the suction pump 74, the intake port 78 causes resistance to suction. Thus, the negative pressure in the fluid collecting vessel 71 is maintained even after unstopping the fluid path C2. High force of suction can be obtained immediately after starting next suction.

Upon opening the fluid path C2 at a port, intake of outer gas starts at the intake port or conduit 78 into the fluid collecting vessel 71. However, the inside of the fluid collecting vessel 71 is kept decompressed with negative pressure without instantaneous recovery in the pressure, because of the smallness of the diameter of the intake port 78 and the suction of the suction pump 74. During the decompressed state, the fluid path C1 at a port is opened to start suction for a second time. As the negative pressure of the fluid collecting vessel 71 is effective, a great force of suction can be obtained in an initial step of the suction. Note that this is effective particularly if a capacity of suction of the suction pump 74 is rather small. If the suction pump 74 is stopped, outer gas is let in through the intake port 78 to recover atmospheric pressure in the inside of the fluid collecting vessel 71.

The start and stop of suction through the drain conduit 30 are controlled time-sequentially according to the time sequence of the start and stop of the dispensation through the pipette couple 26. For the assay, the analyte fluid 27 is introduced to the flow channel 16. At the same time, the liquid buffer is drained from the exit end opening 16b. Should the liquid buffer for the measurement stand to left in the fluid reserving chamber 42d, the buffer will flow back to the flow channel 16 by its own weight. This will cause electric noise in the SPR output signals. To prevent a backflow, the buffer for measurement overflown in the fluid reserving chamber 42d must be sucked immediately. Thus, sucking operation through the drain conduit 30 is started before the start of the dispensation through the pipette couple 26.

In contrast, after stopping dispensation of the analyte fluid 27 from the pipette couple 26, the suction is stopped. If the suction continues even after dispensation, the analyte fluid 27 might be sucked also with a portion which must remain in the flow channel 16.

Although the suction is turned on and off according to the above construction, it is possible to control the extent of the force of the suction between high and low levels without interrupting the continuous suction. Specifically, force of the suction can be set high before the start of the dispensation through the pipette couple 26, and set low at the same time as the stop of the dispensation.

Note that there is a clearance of approximately 1 mm between the exit end opening 16b and the upstream end of the drain conduit 30. Should the drain conduit 30 contact the exit end opening 16b for connection, unwanted suction of the analyte fluid 27 from the middle of the flow channel 16 cannot be prevented no matter how the force of the suction is lowered. In the present invention, the same clearance is ensured to limit the force of suction of the drain conduit 30. The suction of the flow channel 16 from the analyte fluid 27 can be prevented.

Figure 4:
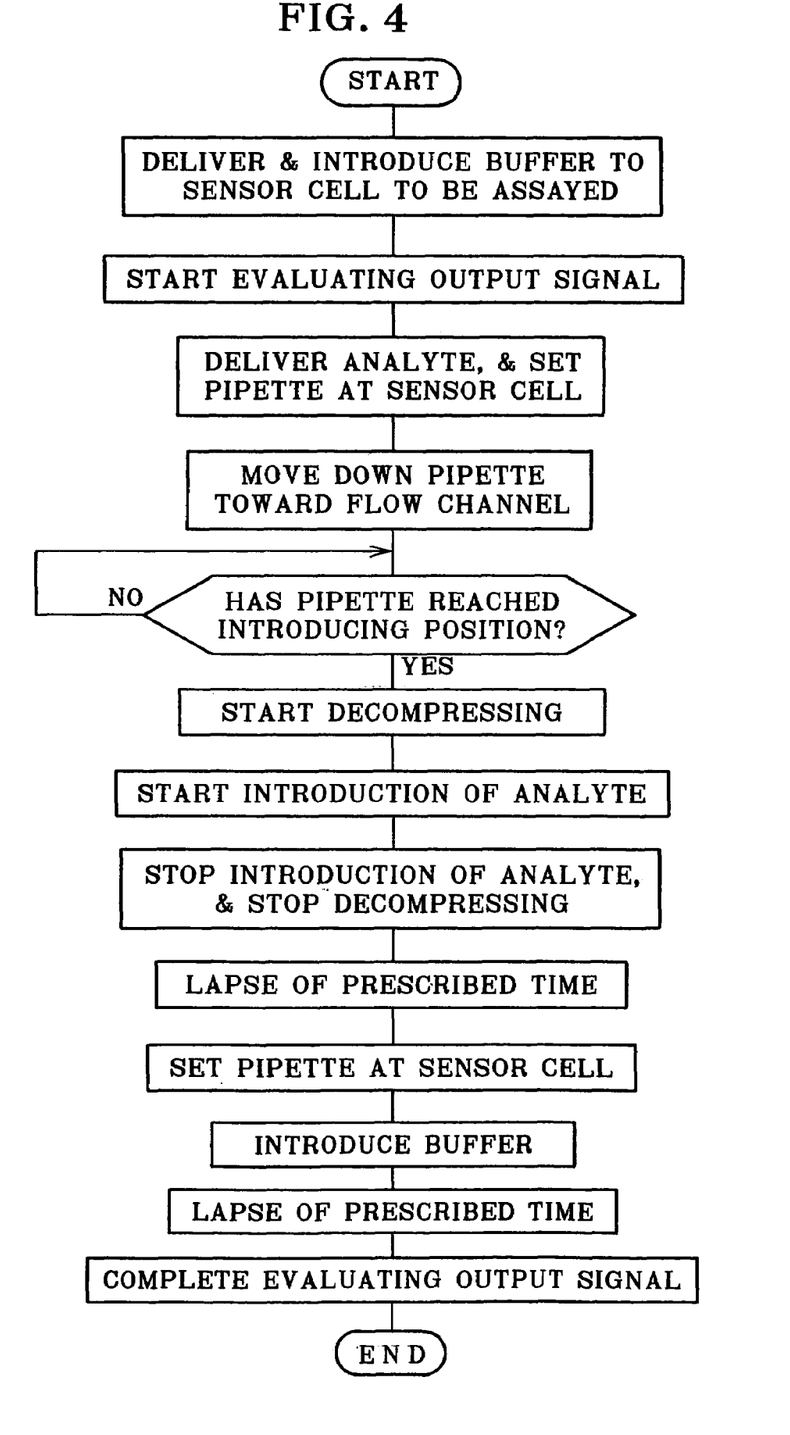
FIG. 4 is a flow chart illustrating the assay method including a process of draining the used sample fluid.

The operation of the above construction is described by referring to FIG. 4. Prior to starting an assay, the pipette couple 26 is supplied with liquid buffer for measurement by a tank. Then the pipette couple 26 shifts to a selected one of the sensor cells 17 to be assayed, and introduces the buffer to the flow channel 16. After the introduction of the buffer, an output signal starts being measured. The pipette couple 26 is supplied with unused analyte liquid by the tank, and shifts to a position higher than the sensor cells 17 to be assayed. The pipette couple 26 starts moving down to the flow channel 16. When the pipette couple 26 reaches the dispensing position, the upstream end of the drain conduit 30 also reaches the fluid reserving chamber 42*d*.

The controller 60 responds to the detection signal from the photo sensor 66, and recognizes the reach of the pipette couple 26 to the dispensing position. The fluid path C1 is opened, to start suction through the drain conduit 30. The pipette couple 26 ejects the analyte fluid 27 for introduction to the flow channel 16. The introduction of the analyte fluid 27 drains the measuring buffer through the exit end opening 16*b*. However, the suction of the drain conduit 30 prevents the measuring buffer from flowing back to the flow channel 16. Thus, occurrence of electric noise in an output signal is prevented because of backflow is prevented.

When the analyte fluid 27 of a prescribed amount introduces in the flow channel 16, then the dispensation with the pipette couple 26 is stopped. Also, the fluid path C1 is closed to stop the suction. No reduction of the analyte fluid 27 to remain in the flow channel 16 occurs, because of the stop of the suction in the drain conduit 30.

After the analyte fluid 27 is introduced, prescribed time elapses. Then the pipette couple 26 is moved up and positioned directly higher than the sensor cells 17. A tank for containing measuring buffer is accessed by the pipette couple 26 to suck and retrieve the buffer. The pipette couple 26 is moved back to a first one of the sensor cells 17 to be assayed. The pipette couple 26 introduces buffer to the flow channel 16. When prescribed time elapses after the introduction of the buffer, measurement of the output signal is completed. Upon introducing the measuring buffer, an output signal is measured for reaction of dissociation between the analyte and ligand. Thus, the dispensation through the pipette couple 26 and the suction through the drain conduit 30 are synchronized by the control for the purpose of preventing backflow of the used sample fluid or waste fluid 90 in the similar manner to the introduction of the analyte fluid 27. The first one of the sensor cells 17 finishes being assayed. When measurement of a second one of the sensor cells 17 is desired, the pipette couple 26 is moved. The same process follows.

Note that, although the flow of FIG. 4 relates to the analyte fluid 27, the operation with the pipette couple 26 and the drain conduit 30 can apply also to liquids other than the analyte fluid 27, for example liquid buffer for introduction to the flow channel 16. It is possible not to synchronize operation between the pipette couple 26 and the drain conduit 30 at the time not during the measurement of signals. This is because of no occurrence of electrical noise of the signals. However, the sequence in the operation of the pipette couple 26 and the drain conduit 30 is preferably preset irrespective of existence or lack of measuring signals. This can simplify the entirety of the control and can be free from raising the structural cost due to the complexity, because no change is made between the kinds of the fluids owing to the sequence previously determined in view of suitability for the analyte fluid 27.

In the above embodiment, the dispensing pipette in the pipette couple 26 is used for delivery. However, other fluid dispenser may be used, for example a pump.

Note that the sample fluid of which a backflow is prevented is the analyte fluid 27. However, a sample fluid of which a backflow is prevented according to the invention can be ligand fluid. This is effective specifically in measuring a process of immobilization of ligand of the ligand fluid, because electrical noise can be suppressed by preventing a backflow of the ligand fluid.

Furthermore, various known elements may be used for the purpose of preventing a backflow of fluid by suction, for example conduits, a pump, a pressure control device, and the like disclosed in U.S. Pat. No. 4,650,477 (corresponding to JP-A 59-091963). Also, the pump or other suction device for draining fluid can be connected in the manner suggested in U.S. Pat. No. 4,871,683 (corresponding to JP-A 62-502706).

In addition to the SPR sensor, an assay sensor according to the invention can be other sensor in utilizing attenuated total reflection. One example of sensor according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a thin film/dielectric interface on the cladding layer. When light becomes incident on the thin film/dielectric interface to satisfy the condition of the total reflection, part of the light passes through the cladding layer, and enters the optical waveguide layer. A guided mode to propagate light is excited responsively in the optical waveguide layer, to attenuate the reflected light on the thin film/dielectric interface. An angle of the incidence at which the guided mode is excited is changeable according to the refraction index of the medium positioned on the sensing surface. This is similar to the characteristic of the resonance angle of the SPR sensor. The attenuation of the reflected light is detected, so that it is possible to measure the interaction on the sensing surface.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An assay apparatus for assay in utilizing attenuated total reflection by use of a sensor unit including a transparent dielectric medium, and a thin film, having a first surface and a sensing surface reverse thereto, said first surface being connected with said dielectric medium to constitute a thin film/dielectric interface, wherein a flow channel is used, has an entrance end opening and an exit end opening, and causes sample fluid introduced through said entrance end opening to flow on said sensing surface, there being an optical assay unit for traveling of illuminating light to said interface in a form satisfying a total reflection condition, and for assaying reaction of said sample fluid on said sensing surface by detecting attenuation of said illuminated light reflected by said interface, said assay apparatus comprising:
   a fluid dispenser for introducing said sample fluid to said entrance end opening;
   a fluid collecting vessel for storing said sample fluid used and exited from said exit end opening;
   a drain conduit, disposed to extend from said exit end opening toward said fluid collecting vessel, for passage of said used sample fluid; and
   a suction device for draining said used sample fluid into said fluid collecting vessel by suction thereof through said drain conduit.

2. An assay apparatus as defined in claim 1, wherein said suction device prevents said used sample fluid from flowing back through said exit end opening, to suppress decrease in measuring precision of said optical assay unit.

3. An assay apparatus as defined in claim 2, wherein said drain conduit has an upstream end disposed at a predetermined interval from said exit end opening.

4. An assay apparatus as defined in claim 2, wherein said suction device decompresses gas inside said fluid collecting vessel by use of negative pressure for said suction, for said used sample fluid to flow through said drain conduit toward said fluid collecting vessel.

5. An assay apparatus as defined in claim 4, further comprising a controller for controlling said suction device for suction sequentially according to start and stop of said fluid dispenser introducing said sample fluid.

6. An assay apparatus as defined in claim 5, wherein said sensor unit includes a fluid reserving chamber formed to communicate serially with said exit end opening, for reserving said used sample fluid;

wherein said drain conduit has an upstream end disposed within said fluid reserving chamber.

7. An assay apparatus as defined in claim 6, wherein said controller starts said suction device for suction sequentially in compliance with starting of said fluid dispenser to introduce said sample fluid, and stops said suction device from suction sequentially in compliance with stopping of said fluid dispenser from introducing said sample fluid.

8. An assay apparatus as defined in claim 6, wherein said fluid reserving chamber extends in a larger size than said exit end opening.

9. An assay apparatus as defined in claim 4, further comprising a switching valve, connected in a middle of said drain conduit, for opening and closing a conduit cavity where said used sample fluid passes toward said fluid collecting vessel.

10. An assay apparatus as defined in claim 9, further comprising an intake conduit connected to said switching valve for intake of external gas toward said fluid collecting vessel, wherein said switching valve sets a selected one of a first state for opening said drain conduit and closing said intake conduit, and a second state for closing said drain conduit and opening said intake conduit.

11. An assay apparatus as defined in claim 2, wherein said drain conduit is moved and set at said sensor unit together with said fluid dispenser.

12. An assay apparatus as defined in claim 2, said fluid dispenser is a pipetting type.

13. An assay method of assay in utilizing attenuated total reflection by use of a sensor unit including a transparent dielectric medium, and a thin film, having a first surface and a sensing surface reverse thereto, said first surface being connected with said dielectric medium to constitute a thin film/dielectric interface, wherein a flow channel is used, has an entrance end opening and an exit end opening, and causes sample fluid introduced through said entrance end opening to flow on said sensing surface, and an optical assay unit is used for traveling of illuminating light to said interface in a form satisfying a total reflection condition, and for assaying reaction of said sample fluid on said sensing surface by detecting attenuation of said illuminated light reflected by said interface, said assay method comprising steps of:

sucking said sample fluid used and exited from said exit end opening;

draining said used sample fluid sucked to flow into a fluid collecting vessel.

14. An assay method as defined in claim 13, wherein in said sucking step, said used sample fluid is prevented from flowing back through said exit end opening, to suppress decrease in measuring precision of said optical assay unit.

15. An assay method as defined in claim 14, wherein a drain conduit is used and extends from said exit end opening toward said fluid collecting vessel, for passage of said used sample fluid;

said drain conduit has an upstream end disposed at a predetermined interval from said exit end opening.

16. An assay method as defined in claim 15, wherein in said sucking step, gas inside said fluid collecting vessel is decompressed by use of negative pressure for suction, for said used sample fluid to flow through said drain conduit toward said fluid collecting vessel.

17. An assay method as defined in claim 16, wherein a fluid reserving chamber is formed to communicate serially with said exit end opening, and reserves said used sample fluid, and said drain conduit causes said used sample fluid from said fluid reserving chamber to flow.

18. An assay method as defined in claim 15, wherein said sucking step is started sequentially in compliance with starting of introduction of said sample fluid, and is stopped sequentially in compliance with stopping of said introduction of said sample fluid.

* * * * *